US 8,457,706 B2

(12) United States Patent
Baker, Jr.

(10) Patent No.: US 8,457,706 B2
(45) Date of Patent: Jun. 4, 2013

(54) ESTIMATION OF A PHYSIOLOGICAL PARAMETER USING A NEURAL NETWORK

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1049 days.

(21) Appl. No.: 12/467,013

(22) Filed: May 15, 2009

(65) Prior Publication Data

US 2009/0287070 A1    Nov. 19, 2009

Related U.S. Application Data

(60) Provisional application No. 61/053,827, filed on May 16, 2008.

(51) Int. Cl.
*A61B 5/00* (2006.01)
(52) U.S. Cl.
USPC ........................................................ 600/323
(58) Field of Classification Search
USPC .............. 600/309, 310, 300, 481, 502, 323, 600/324; 367/155
See application file for complete search history.

(56) References Cited

U.S. PATENT DOCUMENTS

| | | | |
|---|---|---|---|
| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,527,557 A | 7/1985 | DeVries et al. |
| 4,939,647 A | 7/1990 | Clough et al. |
| 4,957,107 A | 9/1990 | Sipin |
| 4,971,052 A | 11/1990 | Edwards |
| 4,986,268 A | 1/1991 | Tehrani |
| 4,991,576 A | 2/1991 | Henkin et al. |
| 4,993,269 A | 2/1991 | Guillaume et al. |
| 5,000,173 A | 3/1991 | Zalkin et al. |
| 5,094,235 A | 3/1992 | Westenskow et al. |
| 5,109,838 A | 5/1992 | Elam |
| 5,127,400 A | 7/1992 | DeVries et al. |
| 5,134,995 A | 8/1992 | Grunke et al. |
| 5,161,525 A | 11/1992 | Kimm et al. |
| 5,168,868 A | 12/1992 | Hicks |
| 5,178,155 A | 1/1993 | Mault |
| 5,237,987 A | 8/1993 | Anderson et al. |
| 5,255,675 A | 10/1993 | Kolobow |
| 5,259,373 A | 11/1993 | Grunke et al. |
| 5,269,293 A | 12/1993 | Löser et al. |

(Continued)

FOREIGN PATENT DOCUMENTS

| EP | 1 205 203 | 9/2004 |
|---|---|---|
| EP | 1 189 649 | 6/2005 |

(Continued)

OTHER PUBLICATIONS

Dowla et al, Neural Networks and Wavelet Analysis in the Computer Interpretation of Pulse Oximetry Data, Lawrence Livermore Laboratory, University of California, pp. 527-536, 1996.*

*Primary Examiner* — Brian Szmal (57) ABSTRACT

A neural network is used to combine one or more estimates of a physiologic parameter with one or more associated signal quality metrics, creating a more accurate estimate of said physiologic parameter, as well as a second estimate of the accuracy of said physiologic parameter estimate.

17 Claims, 7 Drawing Sheets

U.S. PATENT DOCUMENTS

| | | | |
|---|---|---|---|
| 5,277,175 A | 1/1994 | Riggs et al. | |
| 5,299,568 A | 4/1994 | Forare et al. | |
| 5,301,667 A | 4/1994 | McGrail et al. | |
| 5,309,901 A | 5/1994 | Beaussant | |
| 5,315,989 A | 5/1994 | Tobia | |
| 5,331,995 A | 7/1994 | Westfall et al. | |
| 5,339,807 A | 8/1994 | Carter | |
| 5,343,858 A | 9/1994 | Winefordner et al. | |
| 5,365,922 A | 11/1994 | Raemer | |
| 5,368,021 A | 11/1994 | Beard et al. | |
| 5,383,449 A | 1/1995 | Forare et al. | |
| 5,388,575 A | 2/1995 | Taube | |
| 5,390,666 A | 2/1995 | Kimm et al. | |
| 5,398,677 A | 3/1995 | Smith | |
| 5,398,682 A | 3/1995 | Lynn | |
| 5,429,123 A | 7/1995 | Shaffer et al. | |
| 5,452,714 A | 9/1995 | Anderson et al. | |
| 5,467,766 A | 11/1995 | Ansite et al. | |
| 5,494,028 A | 2/1996 | DeVries et al. | |
| 5,497,767 A | 3/1996 | Olsson et al. | |
| 5,503,140 A | 4/1996 | Winefordner et al. | |
| 5,503,147 A | 4/1996 | Bertheau | |
| 5,517,983 A | 5/1996 | Deighan et al. | |
| 5,524,615 A | 6/1996 | Power | |
| 5,535,738 A | 7/1996 | Estes et al. | |
| 5,540,220 A | 7/1996 | Gropper et al. | |
| 5,542,416 A | 8/1996 | Chalvignac | |
| 5,546,935 A | 8/1996 | Champeau | |
| 5,549,106 A | 8/1996 | Gruenke et al. | |
| 5,551,419 A | 9/1996 | Froehlich et al. | |
| 5,568,910 A | 10/1996 | Koehler et al. | |
| 5,575,283 A | 11/1996 | Sjoestrand | |
| 5,605,151 A | 2/1997 | Lynn | |
| 5,606,968 A | 3/1997 | Mang | |
| 5,617,847 A | 4/1997 | Howe | |
| 5,623,923 A | 4/1997 | Bertheau et al. | |
| 5,632,270 A | 5/1997 | O'Mahony et al. | |
| 5,657,750 A | 8/1997 | Colman et al. | |
| 5,660,171 A | 8/1997 | Kimm et al. | |
| 5,662,099 A | 9/1997 | Tobia et al. | |
| 5,678,537 A | 10/1997 | Bathe et al. | |
| 5,692,497 A | 12/1997 | Schnitzer et al. | |
| 5,697,363 A | 12/1997 | Hart | |
| 5,701,883 A | 12/1997 | Hete et al. | |
| 5,701,889 A | 12/1997 | Danon | |
| 5,752,509 A | 5/1998 | Lachmann et al. | |
| 5,771,884 A | 6/1998 | Yarnall et al. | |
| 5,794,614 A | 8/1998 | Gruenke et al. | |
| 5,797,393 A | 8/1998 | Kohl | |
| 5,803,064 A | 9/1998 | Phelps et al. | |
| 5,813,399 A | 9/1998 | Isaza et al. | |
| 5,823,179 A | 10/1998 | Grychowski et al. | |
| 5,826,575 A | 10/1998 | Lall | |
| 5,845,636 A | 12/1998 | Gruenke et al. | |
| 5,853,364 A * | 12/1998 | Baker et al. | 600/300 |
| 5,857,458 A | 1/1999 | Tham et al. | |
| 5,868,133 A | 2/1999 | DeVries et al. | |
| 5,875,783 A | 3/1999 | Kullik | |
| 5,876,352 A | 3/1999 | Weismann | |
| 5,881,717 A | 3/1999 | Isaza | |
| 5,881,722 A | 3/1999 | DeVries et al. | |
| 5,891,023 A | 4/1999 | Lynn | |
| 5,918,597 A | 7/1999 | Jones et al. | |
| 5,937,856 A | 8/1999 | Jonasson et al. | |
| 5,957,130 A | 9/1999 | Krahbichler et al. | |
| 6,002,952 A * | 12/1999 | Diab et al. | 600/310 |
| 6,041,777 A | 3/2000 | Faithfull et al. | |
| 6,095,139 A | 8/2000 | Psaros | |
| 6,095,140 A | 8/2000 | Poon et al. | |
| 6,102,038 A | 8/2000 | DeVries | |
| 6,119,686 A | 9/2000 | Somerson et al. | |
| 6,123,074 A | 9/2000 | Hete et al. | |
| 6,131,571 A | 10/2000 | Lampotang et al. | |
| 6,135,967 A | 10/2000 | Fiorenza et al. | |
| 6,148,814 A | 11/2000 | Clemmer et al. | |
| 6,152,132 A | 11/2000 | Psaros | |
| 6,152,135 A | 11/2000 | DeVries et al. | |
| 6,158,432 A | 12/2000 | Biondi et al. | |
| 6,176,234 B1 | 1/2001 | Salter et al. | |
| 6,192,885 B1 | 2/2001 | Jalde | |
| 6,217,524 B1 | 4/2001 | Orr et al. | |
| 6,223,064 B1 | 4/2001 | Lynn et al. | |
| 6,287,264 B1 | 9/2001 | Hoffman | |
| 6,295,330 B1 | 9/2001 | Skog et al. | |
| 6,295,985 B1 | 10/2001 | Kock et al. | |
| 6,306,098 B1 | 10/2001 | Orr et al. | |
| 6,308,706 B1 | 10/2001 | Lammers et al. | |
| 6,309,360 B1 | 10/2001 | Mault | |
| 6,321,748 B1 | 11/2001 | O'Mahoney | |
| 6,342,039 B1 | 1/2002 | Lynn et al. | |
| 6,349,922 B1 | 2/2002 | Rydin | |
| 6,371,113 B1 | 4/2002 | Tobia et al. | |
| 6,371,114 B1 | 4/2002 | Schmidt et al. | |
| 6,390,091 B1 | 5/2002 | Banner et al. | |
| 6,412,483 B1 | 7/2002 | Jones et al. | |
| 6,415,788 B1 | 7/2002 | Clawson et al. | |
| 6,419,634 B1 | 7/2002 | Gaston, IV et al. | |
| 6,457,472 B1 | 10/2002 | Schwartz et al. | |
| 6,512,938 B2 | 1/2003 | Claure et al. | |
| 6,523,537 B1 | 2/2003 | Mas Marfany | |
| 6,523,538 B1 | 2/2003 | Wikefeldt | |
| 6,526,970 B2 | 3/2003 | DeVries et al. | |
| 6,532,958 B1 | 3/2003 | Buan et al. | |
| 6,532,959 B1 | 3/2003 | Berthon-Jones | |
| 6,532,960 B1 | 3/2003 | Yurko | |
| 6,536,429 B1 | 3/2003 | Pavlov et al. | |
| 6,543,449 B1 | 4/2003 | Woodring et al. | |
| 6,550,479 B1 | 4/2003 | Duxbury | |
| 6,557,553 B1 | 5/2003 | Borrello | |
| 6,557,554 B1 | 5/2003 | Sugiura | |
| 6,561,187 B2 | 5/2003 | Schmidt et al. | |
| 6,564,798 B1 | 5/2003 | Jalde | |
| 6,572,561 B2 | 6/2003 | Mault | |
| 6,575,164 B1 | 6/2003 | Jaffe et al. | |
| 6,575,165 B1 | 6/2003 | Cook et al. | |
| 6,575,918 B2 | 6/2003 | Kline | |
| 6,584,973 B1 | 7/2003 | Biondi et al. | |
| 6,606,994 B1 | 8/2003 | Clark | |
| 6,609,016 B1 | 8/2003 | Lynn | |
| 6,616,615 B2 | 9/2003 | Mault | |
| 6,619,289 B1 | 9/2003 | Mashak | |
| 6,622,725 B1 | 9/2003 | Fisher et al. | |
| 6,629,934 B2 | 10/2003 | Mault et al. | |
| 6,631,716 B1 | 10/2003 | Robinson et al. | |
| 6,640,806 B2 | 11/2003 | Yurko | |
| 6,644,312 B2 | 11/2003 | Berthon-Jones et al. | |
| 6,668,824 B1 | 12/2003 | Isaza et al. | |
| 6,671,529 B2 | 12/2003 | Claure et al. | |
| 6,688,307 B2 | 2/2004 | Berthon-Jones | |
| 6,722,359 B2 | 4/2004 | Chalvignac | |
| 6,723,055 B2 | 4/2004 | Hoffman | |
| 6,729,331 B2 | 5/2004 | Kay | |
| 6,739,334 B2 | 5/2004 | Valeij | |
| 6,748,252 B2 | 6/2004 | Lynn et al. | |
| 6,752,151 B2 | 6/2004 | Hill | |
| 6,758,216 B1 | 7/2004 | Berthon-Jones et al. | |
| 6,760,608 B2 | 7/2004 | Lynn | |
| 6,761,165 B2 | 7/2004 | Strickland, Jr. | |
| 6,763,829 B2 | 7/2004 | Jaffe et al. | |
| 6,772,762 B2 | 8/2004 | Piesinger | |
| 6,796,305 B1 | 9/2004 | Banner et al. | |
| 6,805,121 B1 | 10/2004 | Flood et al. | |
| 6,820,618 B2 | 11/2004 | Banner et al. | |
| 6,837,242 B2 | 1/2005 | Younes | |
| 6,868,346 B2 | 3/2005 | Larson et al. | |
| 6,877,511 B2 | 4/2005 | DeVries et al. | |
| 6,886,558 B2 | 5/2005 | Tanaka | |
| 6,896,713 B1 | 5/2005 | Eckerbom et al. | |
| 6,938,619 B1 | 9/2005 | Hickle | |
| 7,008,380 B1 | 3/2006 | Rees et al. | |
| 7,032,589 B2 | 4/2006 | Kerechanin, II et al. | |
| 7,040,315 B1 | 5/2006 | Strömberg | |
| 7,040,321 B2 | 5/2006 | Göbel | |
| 7,043,979 B2 | 5/2006 | Smith et al. | |
| 7,066,173 B2 | 6/2006 | Banner et al. | |
| 7,066,175 B2 | 6/2006 | Hamilton et al. | |
| 7,081,095 B2 | 7/2006 | Lynn et al. | |

| Patent/Pub No. | Date | Name |
|---|---|---|
| RE39,225 E | 8/2006 | Isaza et al. |
| 7,089,936 B2 | 8/2006 | Madaus et al. |
| 7,092,757 B2 | 8/2006 | Larson et al. |
| 7,100,609 B2 | 9/2006 | Berthon-Jones et al. |
| 7,118,537 B2 | 10/2006 | Baddour |
| 7,121,277 B2 | 10/2006 | Ström |
| 7,152,598 B2 | 12/2006 | Morris et al. |
| 7,152,604 B2 | 12/2006 | Hickle et al. |
| 7,168,597 B1 | 1/2007 | Jones et al. |
| 7,195,013 B2 | 3/2007 | Lurie |
| 7,210,478 B2 | 5/2007 | Banner et al. |
| 7,222,623 B2 | 5/2007 | DeVries et al. |
| 7,229,430 B2 | 6/2007 | Hickle et al. |
| 7,241,269 B2 | 7/2007 | McCawley et al. |
| 7,267,122 B2 | 9/2007 | Hill |
| 7,275,540 B2 | 10/2007 | Bolam et al. |
| 7,291,115 B2 | 11/2007 | Cardona Burrul |
| 7,296,573 B2 | 11/2007 | Estes et al. |
| 7,297,119 B2 | 11/2007 | Westbrook et al. |
| 7,302,949 B2 | 12/2007 | Pelerossi et al. |
| 7,320,321 B2 | 1/2008 | Pranger et al. |
| 7,331,343 B2 | 2/2008 | Schmidt et al. |
| 7,347,825 B2 | 3/2008 | Vaughan et al. |
| 7,353,824 B1 | 4/2008 | Forsyth et al. |
| 7,392,806 B2 | 7/2008 | Yuen et al. |
| 7,398,115 B2 | 7/2008 | Lynn |
| 7,406,870 B2 | 8/2008 | Seto |
| 7,448,381 B2 | 11/2008 | Sasaki et al. |
| 7,455,583 B2 | 11/2008 | Taya et al. |
| 7,475,685 B2 | 1/2009 | Dietz et al. |
| 7,484,508 B2 | 2/2009 | Younes |
| 7,509,957 B2 | 3/2009 | Duquette et al. |
| 7,525,663 B2 | 4/2009 | Kwok et al. |
| 7,547,285 B2 | 6/2009 | Kline |
| 2002/0026941 A1 | 3/2002 | Biondi et al. |
| 2002/0082512 A1 | 6/2002 | Strom |
| 2002/0138213 A1 | 9/2002 | Mault |
| 2002/0148468 A1 | 10/2002 | Valeij |
| 2002/0185126 A1 | 12/2002 | Krebs |
| 2003/0062045 A1 | 4/2003 | Woodring et al. |
| 2003/0140921 A1 | 7/2003 | Smith et al. |
| 2003/0158466 A1 | 8/2003 | Lynn et al. |
| 2003/0221689 A1 | 12/2003 | Berthon-Jones |
| 2004/0050387 A1 | 3/2004 | Younes |
| 2004/0138577 A1 | 7/2004 | Kline |
| 2004/0261793 A1 | 12/2004 | Stromberg et al. |
| 2005/0005936 A1 | 1/2005 | Wondka |
| 2005/0109340 A1 | 5/2005 | Tehrani |
| 2005/0124907 A1 | 6/2005 | Kuck et al. |
| 2005/0139211 A1 | 6/2005 | Alston et al. |
| 2005/0150494 A1 | 7/2005 | DeVries et al. |
| 2005/0172965 A1 | 8/2005 | Thulin |
| 2005/0217671 A1 | 10/2005 | Fisher et al. |
| 2005/0284476 A1 | 12/2005 | Blanch et al. |
| 2006/0112959 A1 | 6/2006 | Mechlenburg et al. |
| 2006/0129054 A1 | 6/2006 | Orr et al. |
| 2006/0130839 A1 | 6/2006 | Bassovich |
| 2006/0144144 A1 | 7/2006 | Seto |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0201507 A1 | 9/2006 | Breen |
| 2006/0235324 A1 | 10/2006 | Lynn |
| 2006/0241708 A1 | 10/2006 | Boute |
| 2006/0243278 A1 | 11/2006 | Hamilton et al. |
| 2006/0249148 A1 | 11/2006 | Younes |
| 2006/0249153 A1 | 11/2006 | DeVries et al. |
| 2006/0264762 A1 | 11/2006 | Starr |
| 2006/0272642 A1 | 12/2006 | Chalvignac |
| 2006/0278223 A1 | 12/2006 | Younes |
| 2007/0000491 A1 | 1/2007 | Chalvignac |
| 2007/0000494 A1 | 1/2007 | Banner et al. |
| 2007/0027375 A1 | 2/2007 | Melker et al. |
| 2007/0028921 A1 | 2/2007 | Banner et al. |
| 2007/0062531 A1 | 3/2007 | Fisher et al. |
| 2007/0068530 A1 | 3/2007 | Pacey |
| 2007/0072541 A1 | 3/2007 | Daniels, II et al. |
| 2007/0073183 A1 | 3/2007 | Kline |
| 2007/0077200 A1 | 4/2007 | Baker |
| 2007/0093721 A1 | 4/2007 | Lynn et al. |
| 2007/0095347 A1 | 5/2007 | Lampotang et al. |
| 2007/0113854 A1 | 5/2007 | Mcauliffe |
| 2007/0125377 A1 | 6/2007 | Heinonen et al. |
| 2007/0129647 A1 | 6/2007 | Lynn |
| 2007/0144521 A1 | 6/2007 | DeVries et al. |
| 2007/0144523 A1 | 6/2007 | Bolam et al. |
| 2007/0149860 A1 | 6/2007 | Lynn et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221221 A1 | 9/2007 | Cooke et al. |
| 2007/0232952 A1 | 10/2007 | Baddour |
| 2007/0240718 A1 | 10/2007 | Daly |
| 2007/0255160 A1 | 11/2007 | Daly |
| 2007/0272241 A1 | 11/2007 | Sanborn et al. |
| 2007/0277823 A1 | 12/2007 | Al-Ali et al. |
| 2008/0000471 A1 | 1/2008 | Bolam et al. |
| 2008/0000479 A1 | 1/2008 | Elaz et al. |
| 2008/0009761 A1 | 1/2008 | Acker et al. |
| 2008/0011300 A1 | 1/2008 | Andreiux |
| 2008/0045825 A1 | 2/2008 | Melker et al. |
| 2008/0053438 A1 | 3/2008 | DeVries et al. |
| 2008/0060646 A1 | 3/2008 | Isaza |
| 2008/0060656 A1 | 3/2008 | Isaza |
| 2008/0066752 A1 | 3/2008 | Baker et al. |
| 2008/0066753 A1 | 3/2008 | Martin et al. |
| 2008/0081974 A1 | 4/2008 | Pav |
| 2008/0135044 A1 | 6/2008 | Freitag et al. |
| 2008/0168990 A1 | 7/2008 | Cooke et al. |
| 2008/0178880 A1 | 7/2008 | Christopher et al. |
| 2008/0178882 A1 | 7/2008 | Christopher et al. |
| 2008/0183094 A1 | 7/2008 | Schonfuss et al. |
| 2008/0196720 A1 | 8/2008 | Kollmeyer et al. |
| 2008/0200775 A1 | 8/2008 | Lynn |
| 2008/0200819 A1 | 8/2008 | Lynn et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0251079 A1 | 10/2008 | Richey |
| 2008/0257349 A1 | 10/2008 | Hedner et al. |
| 2009/0171226 A1 | 7/2009 | Campbell et al. |
| 2009/0235935 A1 | 9/2009 | Pacey |

FOREIGN PATENT DOCUMENTS

| | | |
|---|---|---|
| EP | 0 965 357 | 3/2007 |
| WO | WO04000114 | 12/2003 |
| WO | WO2007145948 | 12/2007 |

* cited by examiner

ESTIMATION OF A PHYSIOLOGICAL PARAMETER USING A NEURAL NETWORK

RELATED APPLICATION

This application claims priority from U.S. Provisional Application No. 61/053,827, filed, May 16, 2008, which is hereby incorporated by reference herein in its entirety.

BACKGROUND

In medicine, a plethysmograph is an instrument that measures physiological parameters, such as variations in the size of an organ or body part, through an analysis of the blood passing through or present in the targeted body part, or a depiction of these variations. An oximeter is an instrument that determines the oxygen saturation of the blood. One common type of oximeter is a pulse oximeter, which determines oxygen saturation by analysis of an optically sensed plethysmograph.

A pulse oximeter is a medical device that indirectly measures the oxygen saturation of a patients blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient.

A pulse oximeter may include a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths at different points in the pulse cycle, it is possible to estimate the blood oxygen saturation of hemoglobin in arterial blood. This relies on the observation that highly oxygenated blood will absorb relatively less red light and more infrared light than blood with lower oxygen saturation.

SUMMARY

This disclosure describes systems and methods for using a neural network to improve the accuracy of a measured physiological parameter, such as the pulsatile oxygen saturation ($SpO_2$) measurement generated by a pulse oximeter. As discussed in greater detail below, the disclosure describes the training and use of backpropagation neural networks to calculate an improved estimate of a patient's $SpO_2$ or pulse rate, or the accuracy of the estimate. The backpropagation neural networks were fully interconnected, with bias, using linear or logarithmic sigmoid transfer functions, and typically contained 3 or 4 hidden nodes. In the examples, the improved estimates where obtained by inputting one or more existing parameter estimates and signal quality metrics into the neural network.

One aspect of the disclosure is a method for determining the oxygen saturation of the blood of a patient. The method includes estimating a physiologic parameter from an electronic signal, in which the physiological parameter may be the oxygen saturation estimated from the data supplied by a pulse oximetry sensor. The method also includes calculating one or more signal quality metrics of the electronic signal and then inputting information into a neural network. The information input into the neural networks includes the estimated physiologic parameter and/or at least one signal quality metric. The neural network then calculates at least one output datum, wherein the output datum is representative of the oxygen saturation of the blood of the patient. The output of the neural network is then received and used as the estimated value for the oxygen saturation of the blood of the patient.

Another aspect of the disclosure is a pulse oximeter that incorporates a neural network for the calculation of blood oxygen saturation. The pulse oximeter includes: a microprocessor capable of calculating an estimated value of oxygen saturation of a patient's blood at least in part upon information received from a sensor; a neural network module capable of receiving the estimated value as an input and calculating a revised value of oxygen saturation of a patient's blood using a neural network; and a display capable of displaying the revised value of the oxygen saturation of the patient's blood. The pulse oximeter may further include memory storing at least one neural network including the neural network used by the neural network module to calculate the revised value. The neural network in the pulse oximeter may also be capable of receiving the estimated value and at least one signal quality metric.

In yet another aspect, the disclosure describes a method for the real-time display of a physiological parameter. The method includes calculating a first estimated value of the physiological parameter. The first estimated physiological parameter is then input into a previously trained neural network to obtain a second estimated value for the physiological parameter. The second estimated value of the physiological parameter is then displayed as the current value of the physiological parameter.

These and various other features as well as advantages which characterize the disclosed systems and methods will be apparent from a reading of the following detailed description and a review of the associated drawings. Additional features of the systems and methods described herein are set forth in the description which follows, and in part will be apparent from the description, or may be learned by practice of the technology. The benefits and features will be realized and attained by the structure particularly pointed out in the written description and claims as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

Challenging monitoring conditions, such as motion or low perfusion, are known to degrade the accuracy of pulse oximeters. Modern pulse oximetry algorithms contain numerous signal quality metrics that are used to modify the behavior of said algorithm in the presence of challenging conditions. This disclosure describes the training and use of backpropagation neural networks to calculate an improved estimate of physiological parameters such as a patient's pulsatile oxygen saturation, pulse rate, or the accuracy of the estimate. The backpropagation neural nets were fully interconnected, with bias, using linear or logarithmic sigmoid transfer functions, and typically contained 3 or 4 hidden nodes in a single hidden layer. In the examples, the improved estimates where obtained by inputting one or more existing parameter estimates and signal quality metrics into the neural network.

Although the techniques for calculating physiological parameters using neural networks introduced above and discussed in detail below may be implemented for a variety of medical devices and physiological parameters, the present disclosure will discuss the implementation of these techniques in a pulse oximeter. Although described in detail in this context of a pulse oximeter displaying oxygen saturation measurements, the reader will understand that the systems and methods described herein may be equally adapted to the estimation and display of any physiological parameter of any patient (human or non-human) generated by any monitoring device, including but not limited to pulse rate, blood pressure, temperature, cardiac output, respiration parameters, and measures of blood constituents other than oxygenation.

Figure 1:
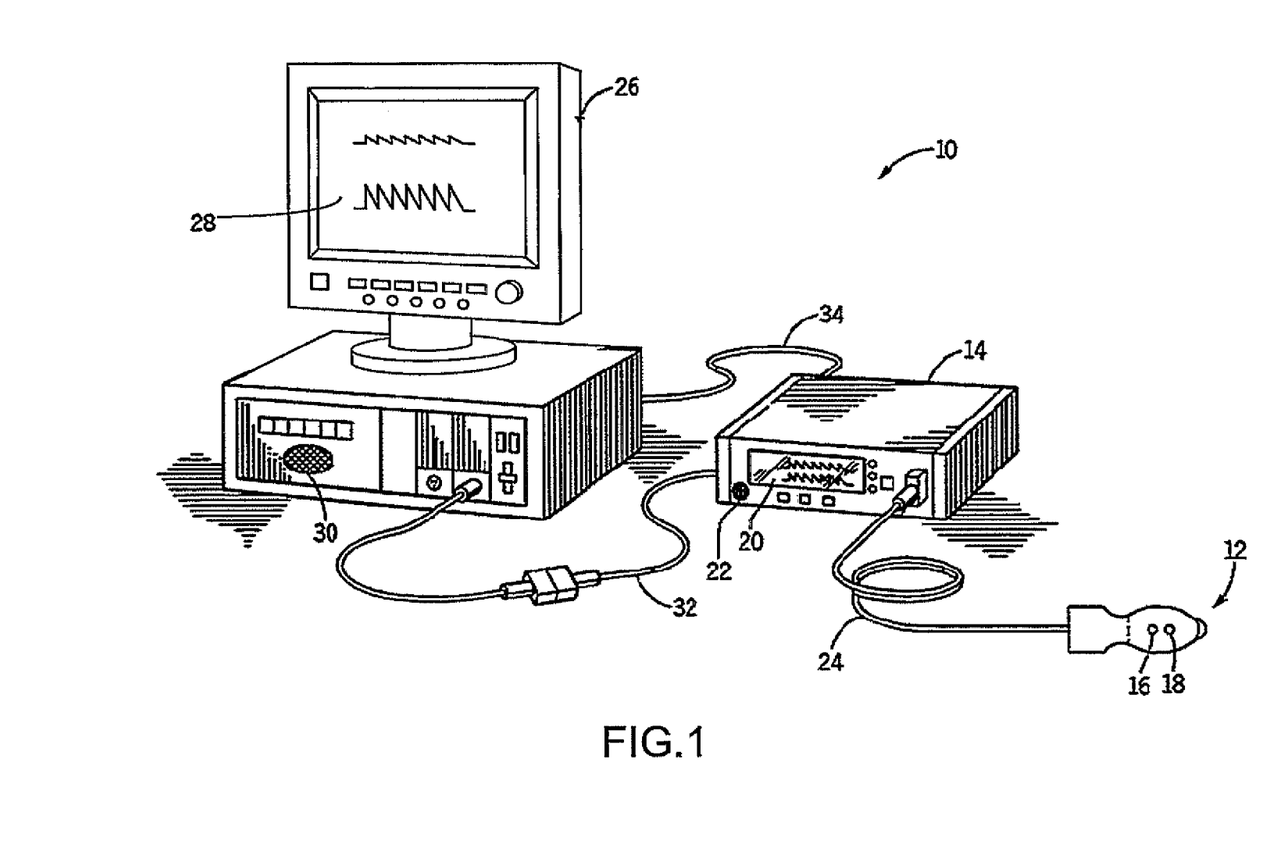
FIG. 1 is a perspective view of a pulse oximetry system.

FIG. 1 is a perspective view of an embodiment of a pulse oximetry system 10. The system 10 includes a sensor 12 and a pulse oximetry monitor 14. The sensor 12 includes an emitter 16 for emitting light at two or more wavelengths into a patient's tissue. A detector 18 is also provided in the sensor 12 for detecting the light originally from the emitter 16 that emanates from the patient's tissue after passing through the tissue. The emitter 16 and detector 18 may be on opposite sides of a digit such as a finger or toe, in which case the light that is emanating from the tissue has passed completely through the digit. In an embodiment, the emitter 16 and detector 18 may be arranged so that light from the emitter 16 penetrates the tissue and is reflected by the tissue into the detector 18, such as a sensor designed to obtain pulse oximetry data from a patient's forehead.

In an embodiment, the sensor may be connected to and draw its power from the monitor 14 as shown. In another embodiment, the sensor may be wirelessly connected to the monitor 14 and include its own battery or similar power supply (not shown). The monitor 14 may be configured to calculate physiological parameters based on data received from the sensor 12 relating to light emission and detection. Further, the monitor 14 includes a display 20 configured to display the physiological parameters, other information about the system, and/or alarm indications. In the embodiment shown, the monitor 14 also includes a speaker 22 to provide an audible alarm in the event that the patient's physiological parameters are not within a normal range, as defined based on patient characteristics.

In an embodiment, the sensor 12 is communicatively coupled to the monitor 14 via a cable 24. However, in other embodiments a wireless transmission device (not shown) or the like may be utilized instead of or in addition to the cable 24.

In the illustrated embodiment the pulse oximetry system 10 also includes a multi-parameter patient monitor 26. The monitor may be cathode ray tube type, a flat panel display (as shown) such as a liquid crystal display (LCD) or a plasma display, or any other type of monitor now known or later developed. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display an estimate of a patient's blood oxygen saturation generated by the pulse oximetry monitor 14 (referred to as a "pulsatile oxygen saturation" or "$SpO_2$" measurement in order distinguish it from a direct measurement of blood oxygen saturation), pulse rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient's physiological parameters are found to be outside of the normal range.

The monitor 14 may be communicatively coupled to the multi-parameter patient monitor 26 via a cable 32 or 34 coupled to a sensor input port or a digital communications port, respectively and/or may communicate wirelessly (not shown). In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2:
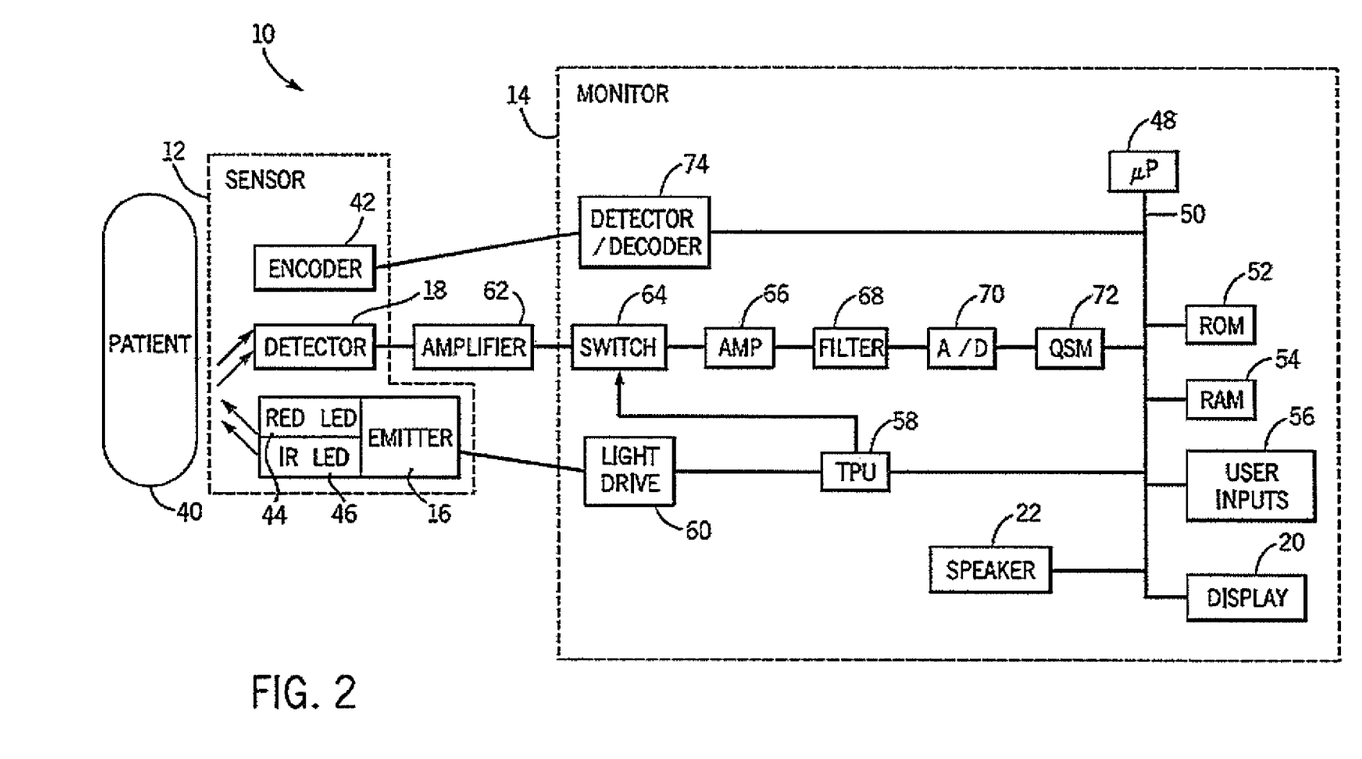
FIG. 2 is a block diagram of the exemplary pulse oximetry system of FIG. 1 coupled to a patient.

FIG. 2 is a block diagram of the embodiment of a pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR light emitting light source such as the IR LED 46 shown for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm.

It should be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein light may also include any wavelength within the radio, microwave, infrared, visible, ultraviolet, or X-ray spectra, and that any suitable wavelength of electromagnetic radiation may be appropriate for use with the present techniques. Similarly, detector 18 may be chosen to be specifically sensitive to the chosen targeted energy spectrum of the light source 16.

In an embodiment, the detector 18 may be configured to detect the intensity of light at the RED and IR wavelengths. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

In an embodiment, the encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40, such as, for example, the patient's age, weight, and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12, the wavelengths of light emitted by the emitter 16, and/or the patient's characteristics. These coded values may be communicated to the monitor 14, which determines how to calculate the patient's physiological parameters and alarm threshold ranges. In another embodiment the encoder 42 may include a memory on which one or more of the following information may be stored for communication to the monitor 14: the type of the sensor 12; the wavelengths of light emitted by the emitter 16; the proper calibration coefficients and/or algorithms to be used for calculating the patient's physiological parameters and/or alarm threshold values; the patient characteristics to be used for calculating the alarm threshold values; and the patient-specific threshold values to be used for monitoring the physiological parameters.

In an embodiment, signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 16 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

In an embodiment, the microprocessor 48 may determine the patient's physiological parameters, such as $SpO_2$ and pulse rate, using various algorithms and/or look-up tables based on the value of the received signals and/or data corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The encoder 42 may also contain the patient-specific alarm thresholds, for example, if the alarm values are determined on a workstation separate from the monitor 14. The user inputs 56 may also be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56. The microprocessor 48 may then determine the proper thresholds using the user input data and algorithms stored in the ROM 52. The patient-specific thresholds may be stored on the RAM 54 for comparison to measured physiological parameters.

In embodiments of monitoring systems described in this disclosure, a neural network is used to create a more accurate estimate of a physiological parameter. In addition, the neural network may be used to generate an estimate of the accuracy of said physiologic parameter estimate. For example, in an embodiment the neural network is used to combine one or more estimates of a physiologic parameter with one or more associated signal quality metrics, creating a more accurate estimate of said physiologic parameter.

It should be noted that, when a neural network is used to combine two or more input estimates of a physiologic parameter, a neural network is not performing a simple selection or interpolation between the two input parameters. Rather, the neural network, during the process of training, creates a non-linear and complex model that generates an output based on all the inputs.

Figure 3:
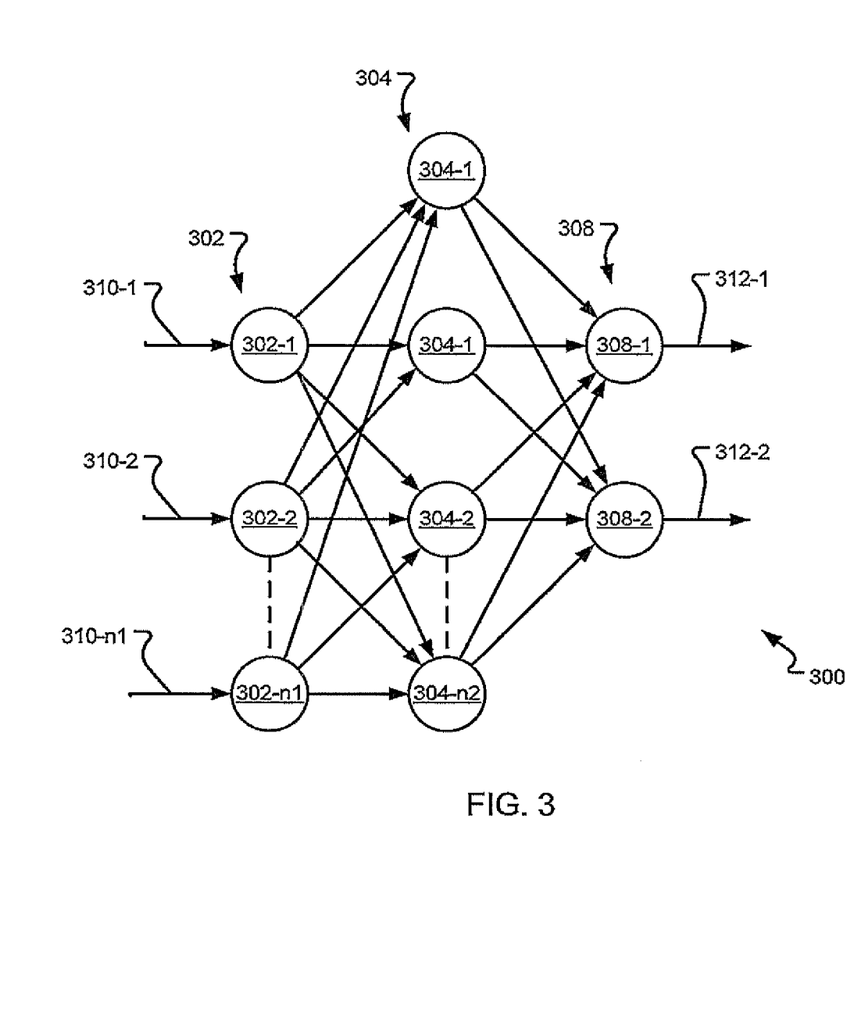
FIG. 3 illustrates an embodiment of a neural network.

FIG. 3 illustrates an embodiment of a neural network. The neural network 300 is represented diagrammatically as a series of interconnected nodes. The references 302, 304, 308 designate various network layers, including an input layer 302, an output layer 308 and a hidden layer 304. In FIG. 3 only one hidden layer is represented, but in alternative embodiments the network may comprise two or more hidden layers, each having any number of hidden nodes. In the embodiment shown, the output layer 308 delivers the estimated physiological parameter, in this case $SpO_2$, in an output 312-1. A second output 312-2 is also illustrated, such as would deliver an estimated accuracy. Depending on the embodiment, the outputs 312 and inputs 310 may be single values or may represent ongoing streams of data.

Each layer k comprises a certain number of nodes, which may alternatively be referred to as synapses. In the embodiment 300 illustrated, there are n1 nodes in layer 302, n2 nodes in layer 304, and 2 nodes in the output layer 308. The input data (processed data) are introduced into the nodes of the input layer 302 at the inputs 310 as shown.

To each node of the neural network 300 there corresponds a function F, which may be a nonlinear activation function such as a hyperbolic tangent function or a sigmoid function, as well as an activation level. Moreover, in the embodiment shown each node i of each layer is linked to the nodes j of the next layer; and a weighting Pij weights each link between a node i and a node j. This weighting weights the influence of the result of each node i in the calculation of the result delivered by each node j to which it is linked.

The output Sj from a node j is equal to the value of the activation function Fj applied to the weighted sum, by the weights Pij of the nodes, of the results Ai of the activation functions of the nodes i which are connected to it. Stated otherwise:

$$Sj = Fj(\Sigma Pij \times Ai)$$

The network 300 represented in FIG. 3 is an open network. In a looped network embodiment, one of the output data 312 is reused as input datum 310.

The work entitled "Modelisation, Classification et Commande par Reseaux de Neurones": Methodologie de Conception et Illustrations Industrielles" [Modelling, Classification and Control using Neural Networks Design Methodology and Industrial Illustrations] by I. Rivals, L. Personnaz, G. Dreyfis, J. L. Ploix (Les Reseaux de Neurones pour la Modelisation et la Commande de Procedes [Neural Networks for Process Modelling and Control], J. P. Corriou, coordinator, Lavoisier Tee et Doc 1995) gives additional information about neural networks.

FIG. 3 illustrates just one embodiment of a neural network 300. Alternative embodiments having more or fewer nodes, more or fewer layers, and in which the network has a different configuration of nodes or interconnections are also possible and considered within the scope of this specification.

In order to generate a more accurate output, a neural network 300 may be trained using actual data. In embodiments, measured data from a physiological parameter monitoring system are selected and used as inputs to train the neural network 300. When selecting the data and parameters to use as inputs, it is preferable to select parameters that are relevant to the output parameter and nonredundant. Relevance means that the information contained in each of the input data contributes to the formation of the result (the output parameter). The mathematical form of this contribution need not be known in order to obtain this result. Non-redundancy means that the correlations between the selected inputs are small.

In some instances depending on the parameter being estimated by the neural network 300, it may further be possible to identify a complete set of inputs 310 for generating the output parameter 312. Completeness means that all the information required to produce a neural network is present in the suite of data.

The processing of the data with a view to creating a neural network 300 involves acquiring raw or physical data regarding the parameter to be estimated. This acquisition preferably covers the entire range of operating conditions over which one wishes the system to be able to predict.

Figure 4:
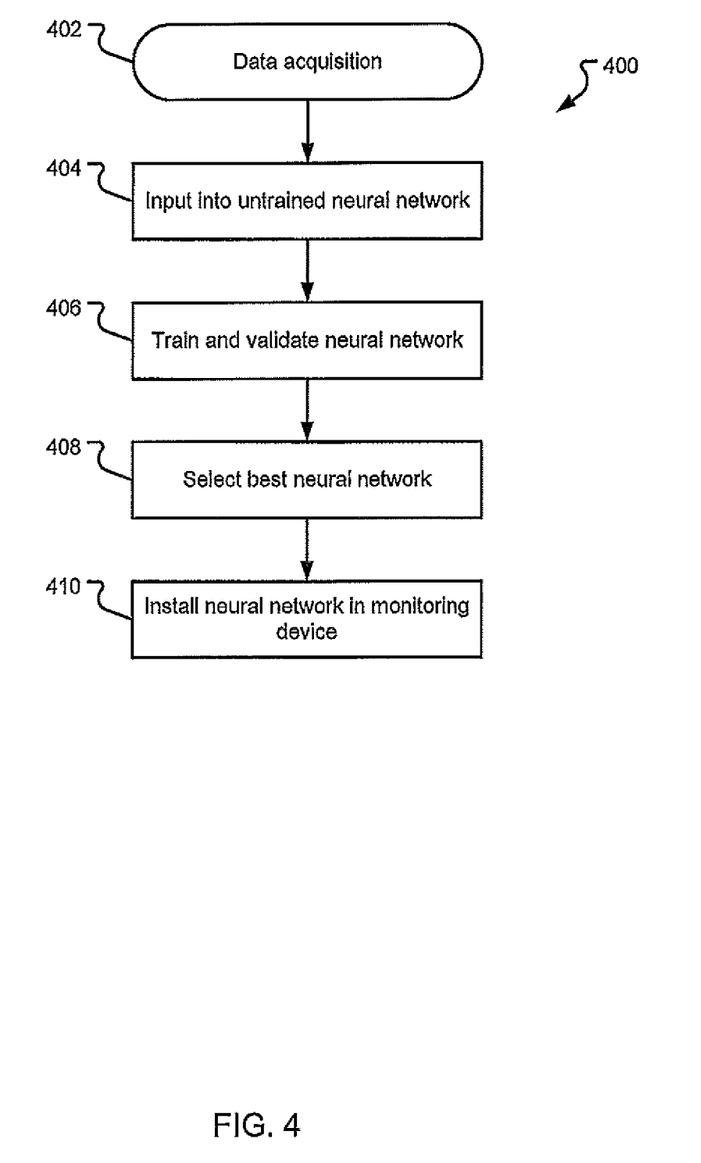
FIG. 4 illustrates an embodiment of a method of creating a neural network for use in estimating physiological parameters.

FIG. 4 illustrates an embodiment of a method of creating a neural network for use in estimating physiological parameters. In the embodiment shown, the method 400 starts with a data acquisition operation 402. In the operation 402, raw data are measured from one or more patients for various potential inputs to the neural network. The data may include raw data obtained from different kinds of sensors monitoring the patients. Such data may also include processed data such as metrics describing one or more parameters of the quality of the raw data obtained from sensors. Processed data may further include estimates of the physiological parameter generated from the raw sensor data. For example, in a neural network created for use in estimating $SpO_2$, many different metrics, parameters or data streams may be used, some of which are presented in TABLE 1 in the Examples.

The data acquisition operation 402 may also include the acquisition of control data to be used as part of the training of the neural network. In an embodiment, the control data may include direct measurements of the physiological parameter(s) obtained by a different means or different equipment than that from which the inputs to the neural network are obtained. For example, if the neural network is to predict a particular physiological parameter from data streams that are indirectly related to that parameter, the control data may include direct measurements of the physiological parameter.

Some of the input data are then introduced into a neural network creation software application in an input operation 404. The software then conducts a training operation 406 in which the software uses the input data to create the functions for each of the nodes in the neural network. The control data is used in the training operation 406 in order to tune the output of the neural network to the most accurate it can be given the input data. The training operation 406 may also include a validation phase (not shown) in which some of the original data obtained in the data acquisition operation 402 that was not used to train the neural network is used to validate the neural network's performance.

In the embodiment shown, several different neural networks may be generated or tested during the training operation 406. The method 400, therefore, further includes a selection of the best neural network in a selection operation 408. The selection may be based on hardware limitations, such as processor load in performing the neural network analysis on input data. The selection may also be based on input requirements such as balancing performance against cost of generating the different inputs necessary to obtain the performance. Other criteria may be further considered when selecting the final neural network.

After the final neural network is selected, that network is then incorporated into a monitoring device or devices, such as the pulse oximetry system described above, in an installation operation 410. The neural network may consist of a software routine that can be executed by a general purpose microprocessor or may be a combination of software, firmware and/or specialized hardware. In any case, the monitoring device is further provided with the capability to generate the inputs necessary for the selected neural network. This may include providing particular sensors or other patient monitoring hardware in order to generate any raw patient data necessary to create the inputs for the neural network. In addition, if the inputs include processed data such as data quality metrics, the capability for generating these processed data inputs is also provided in the monitoring device.

Figure 5:
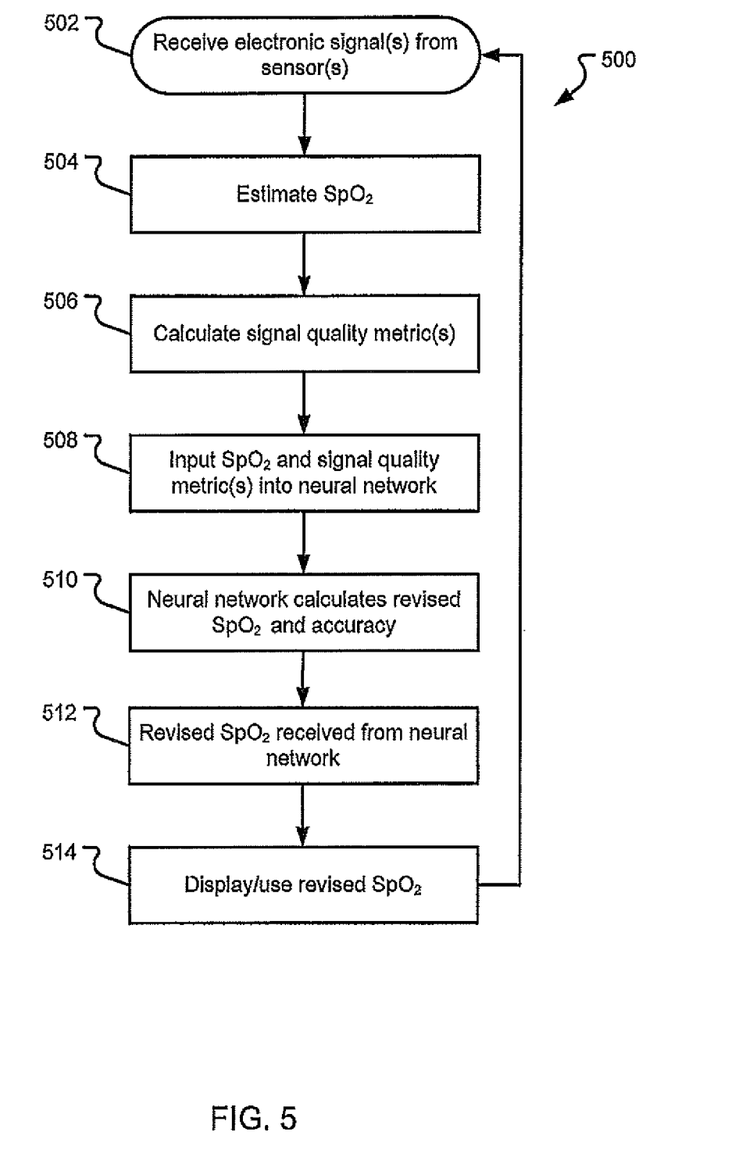
FIG. 5 illustrates an embodiment of a method for estimating a physiological parameter using a neural network.

FIG. 5 illustrates an embodiment of a method for estimating a physiological parameter using a neural network. In the method 500, a trained neural network has been created and provided in a physiological parameter monitoring system such as a pulse oximeter.

In the method 500, the system is monitoring a patient and collecting data from its sensor(s) in a receive data operation 502. In the context of the pulse oximeter described above, the receive data operation 502 includes receiving at least one electronic signal from a sensor indicative of the light received by the detector and processing that signal to generate data that can be processed by the microprocessor. In an embodiment the data, or samples thereof, may be temporarily stored in a buffer to allow multiple analyses of the same data. In additional, some or all of the data may be retained for some period of time for subsequent processing at a later time.

In an embodiment, the received data are analyzed to generate an estimated value of the physiological parameter that is being measured in the generate estimate operation 504. In the context of a pulse oximeter, one physiological parameter estimated is the oxygen saturation of the blood of the patient. In an embodiment, the oxygen saturation of the patients blood is calculated based on the most recent data received from the sensor in order to provide a current measurement of the oxygen saturation. The estimated value of the oxygen saturation may be generated by a sophisticated algorithm and may utilize a significant amount of processor cycles and signal processing hardware (e.g., filters, amplifiers, high-resolution digital to analog converters, etc.). In an embodiment, generation of the estimated value of the oxygen saturation may use statistical information derived from data in the generation of the final estimate. An example of generating an estimated value for oxygen saturation is described in the commonly-assigned U.S. Pat. No. 6,836,679, titled "Method and apparatus for estimating physiological parameters using model-based adaptive filtering". Other methods for generating the estimated value are known in the art and any suitable method, now known or later developed, may be used.

In an embodiment, the generate estimate operation 504 may include estimating more than one parameter including estimating more than one value for the same physiological parameter. Such additional parameter estimates may be made from different sources of data, e.g., data from different sensors, or may be calculated from the same data using different calculation techniques or algorithms.

In an embodiment, in addition to the generation of the estimated parameter value(s), one or more signal quality metrics describing the data are calculated in a calculate metrics operation 506. In the embodiment shown, the calculate metrics operation 506 is performed after the generate estimate operation 504. In embodiments, the metrics may be calculated before, concurrently with or as part of the generate estimate operation 504. Furthermore, the metrics calculated may or may not be used in the calculation of the estimated value and may or may not be calculated by the same module, software application or component of the pulse oximeter that calculates the estimated value. For example, in an embodiment a single software application may be utilized to calculate all metrics and the physiological parameter. In another embodiment, separate and independent software modules or system components may be used to calculate each parameter and/or metric described herein.

One metric that may be determined from the data is a single value representing the accuracy of the estimated value. Accuracy is a well known statistical term of art referring how close an estimated value is likely to be to the actual value based on the errors and limitations of the measurement process and the data obtained. Accuracy can be quantified by many different techniques, including reporting a single value that is a numerical representation of the accuracy of the estimated value. For example, the accuracy of an estimated value of oxygen saturation may be determined by calculating a standard deviation of the physiological data from which the estimated value is determined; the smaller the standard deviation, the greater the accuracy of the estimated value. Thus, the standard deviation itself may be used as a metric representing the accuracy of the estimated value.

In an embodiment, the accuracy of an estimated value may be further determined by more complicated calculations involving a detailed analysis of data received from the sensor. A number of data characteristics potentially indicative of the accuracy of pulse oximetry calculations are known to those skilled in the art. Examples include pulse amplitude, pulse shape, correlation of the IR and RED photoplethysmograph, as well as temporal variations in any of these characteristics. Those skilled in the art of pulse oximeter design will also recognize that multiple data characteristics may be combined empirically in order to more accurately reflect the accuracy of a pulse oximetry system under challenging conditions that may be created experimentally or encountered in clinical usage. Those skilled in the art will also recognize that in order to design such an empirical combination, the accuracy of oxygen saturation and pulse rate measurements under challenging conditions may be independently assessed by techniques such as arterial blood sampling, ECO monitoring, or use of a second pulse oximeter at a different tissue site.

The calculated metrics and estimated parameter(s) are then input into the neural network in an inputting operation 508. The neural network then calculates a revised physiological parameter in calculate revised parameter operation 510. The calculate revised value operation 510 includes calculating the revised physiological parameter(s) and any other outputs that the neural network is designed to generate. For example, as described above in an embodiment the neural network calculates and outputs a revised estimate for $SpO_2$ and a revised accuracy for the $SpO_2$ estimate.

The output or outputs of the neural network are received in a receive output operation 512. In an embodiment, the output revised physiological parameter is received substantially in real time and therefore can be used in place of the estimated value used as an input to the neural network.

In the embodiment shown, the revised $SpO_2$ and the revised accuracy for the $SpO_2$ estimate are received and used by the pulse oximetry system as the most accurate and current values of $SpO_2$ and accuracy in a use neural network output operation 514. Thus, the neural network output may be used in place of the estimated values obtained in the generate estimate operation 504 and the calculate metric(s) operation 506. Such uses may include displaying the revised estimate for $SpO_2$ as the current oxygen saturation of the patient's blood. Such uses may also include generating an alarm if the output revised $SpO_2$ from the neural network is not within an acceptable range of oxygen saturation values.

For example, in an embodiment, after the calculations have been made by the neural network, a display operation may be performed as part of the use neural network output operation 514. In the display portion of the operation 514, the value of the $SpO_2$ output by the neural network may be displayed to a user of the pulse oximeter system, such as a doctor, nurse, other caregiver, or patient. The display may be numerical, graphical or a combination of both in nature. For example, in an embodiment the system generates a graphical user interface (GUI) that is presented on a monitor or other display device that includes some graphical element such as an arrow that indicates the estimated value.

In an embodiment, the method 500 is performed continuously, which is illustrated by the flow returning to the receive data operation 502. That is, data is continually being received, calculations are made from the most recent data and the displayed values are continuously updated. Depending on the implementation, this can be done in a true continuous process or can be done by periodically repeating the operations in FIG. 5 for batches of data received and revising the displayed values after each repetition.

Figure 6:
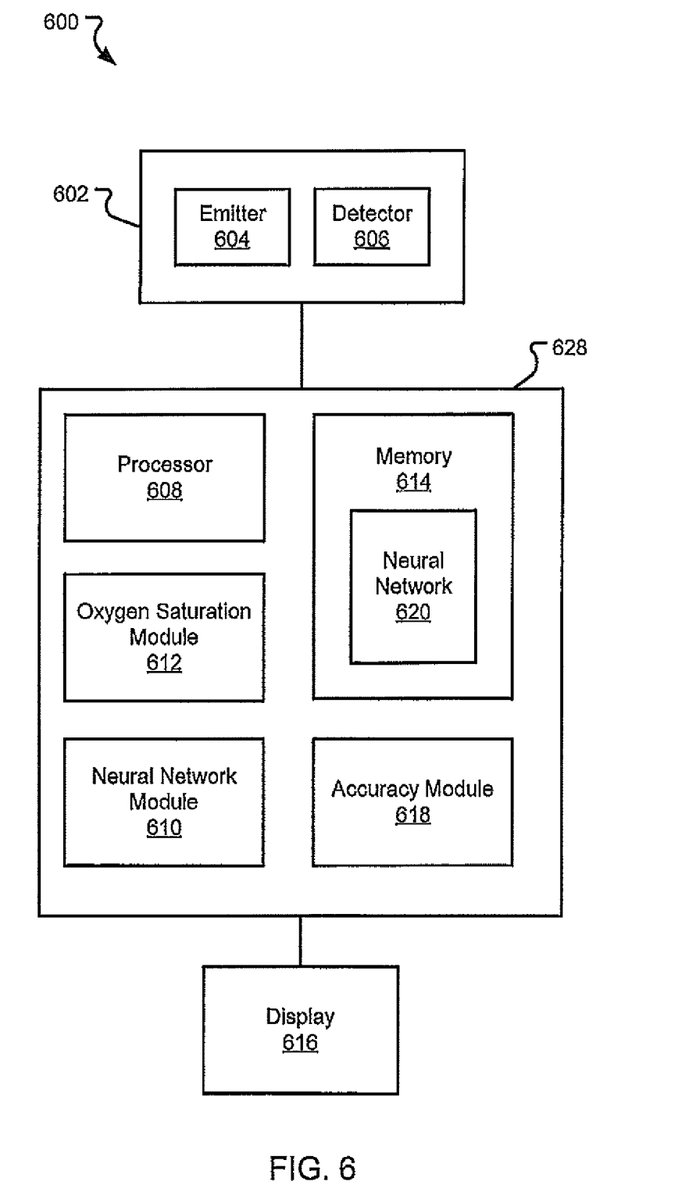
FIG. 6 is a block diagram illustrating some of the components of a pulse oximetry system that uses a neural network to generate a more accurate estimate of the oxygen saturation of a patient's blood.

FIG. 6 is a block diagram illustrating some of the components of a pulse oximetry system that uses a neural network to generate a more accurate estimate of the oxygen saturation of a patient's blood. In the embodiment shown, the system 600 includes a sensor 602 containing a light emitter 604 and a light detector 606; and, in a separate housing 628, a microprocessor 608, a neural network module 610; an oxygen saturation module 612; an accuracy module 618 and a memory 614. A display 616 is also provided. The sensor 602 and its components operate as described previously with reference to FIG. 2.

The memory 614 may include RAM, flash memory or hard disk data storage devices. The memory stores data, which may be filtered or unfiltered data, received from the detector 606. The data may be decimated, compressed or otherwise modified prior to storing in the memory 614 in order to increase the time over which data may be retained. In addition, the memory 614 may also store one or more neural networks 620 (one is shown) for use by the neural network module 610 when calculating an estimated value of the oxygen saturation of a patient's blood. In an embodiment, the stored neural network 620 is a software application that when executed by the microprocessor 608 performs the functions of the neural network module 610 as described herein. In another embodiment the stored neural network 620 represents only the information necessary for dedicated hardware or firmware circuit to perform the functions of the neural network module 610. One skilled in the art will understand that how the neural network is implemented, i.e., as software, firmware, hardware or some combination of the three, is primarily a matter of design choice.

The memory 614 may further store multiple neural networks 620 for use under different conditions. For example, in an embodiment different neural networks may be provided for use with different sensors, for use when different inputs are available, for use under different operational conditions (e.g., when in a high noise environment and a low noise environment) or for use with different patients or patients with different characteristics (e.g., one neural network for trauma patients that are otherwise healthy and one for patients with chronic ailments that directly implicate the patient's blood oxygen saturation).

The oxygen saturation module 612 generates a current oxygen saturation measurement from the data generated by the sensor. This data may be received in the form of an electronic signal from the sensor 602 which may be analog or digital in nature. In the embodiment shown, a separate accuracy module 618 is also illustrated. The accuracy module 618 is capable of calculating the accuracy of the estimated value of the oxygen saturation. This accuracy may then be used as part of the estimation of the oxygen saturation measurement by the oxygen saturation module 612, as an input to the neural network or both.

The neural network module 610 receives the inputs for the neural network, such as the oxygen saturation measurement from the oxygen saturation module 612 and estimated accuracy and calculates the output data. In the embodiment shown, the outputs of the neural network module include a revised estimate of the oxygen saturation and a revised accuracy for the oxygen saturation. If more than one neural networks 620 are available for use by the neural network module 610, it will select the appropriate network 620 based on the current conditions. In an embodiment, the oxygen saturation module 612, neural network module 610 and accuracy module 618 may each be a dedicated hardware circuit that may include filters, firmware comprising lookup tables or other data, and its own processor (not shown) that allow it to generate the revised oxygen saturation measurement using the neural network. A "module" as referred to herein is meant to describe a software, hardware or firmware (or combinations thereof) system, process or functionality that performs or facilitates the processes, features and/or functions described herein (with or without human interaction or augmentation). In an embodiment, the modules may be implemented as a single, combined software application or as separate software applications that are executed, in whole or in part, by the system microprocessor 608. In yet another embodiment, functions described herein as being performed by the oxygen saturation module and modules may be distributed among hardware, software and firmware throughout the system 600 and its other components.

The display 616 may be any device that is capable of generating an audible or visual notification. The display need not be integrated into the other components of the system 600 and could be a wireless device or even a monitor on a general purpose computing device (not shown) that receives email or other transmitted notifications from the housing 628.

EXAMPLES

In the following examples, backpropagation neural networks were used to calculate an improved estimate of a patient's pulsatile oxygen saturation (i.e., $SpO_2$). The backpropagation neural networks used were fully interconnected, with bias, using linear or logarithmic sigmoid transfer functions, and typically contained 3 or 4 hidden nodes in a single hidden layer. In the examples, the improved estimates where obtained by inputting an existing parameter estimate and signal quality metrics into the neural network.

The feasibility of the neural network enhancement is demonstrated in the following examples using data from cold-room motion breathdowns [studies in which volunteers breathed gas mixtures with reduced oxygen content while exposed to room temperature that were cold enough to stimulate vasoconstriction and thereby reduce blood flow in the skin] performed by NELLCOR's clinical studies department. This data was collected on two motion and two non-motion digits using NELLCOR MAX-A sensors, for five different studies, using 12 volunteers in each study. The true $SpO_2$ and pulse rate were estimated as the mean of the values calculated from the two non-motion digits by pulse oximetry algorithm similar to that implemented in the Nellcor N-595 oximeter, subject to manual review and editing. Backpropagation neural networks were trained to approximate these estimates of truth using $SpO_2$, pulse rate, and signal quality metrics obtained by post-processing data from each individual motion and non-motion digit. The estimates of truth covered the range of 60-100% $SpO_2$ and 40-120 beats per minute (BPM). In total, the training data for these neural networks comprise data from 240 digits on 39 unique volunteers (some were in multiple studies). Of these, 120 digits represent various degrees of low perfusion, due to the cold room, while the other 120 digits represent low perfusion in combination with motion.

The table below lists the parameter estimates and signal quality metrics that were evaluated as input to the trained neural nets.

TABLE 1

| Signal Quality Metric | Description |
| --- | --- |
| Kalman Saturation | Saturation obtained by filtering the measured pleth using Kalman filter theory. Described in detail in U.S. Pat. No. 5,853,364. |
| Adaptive Comb Filter (ACF) Rate | The pulse rate as determined using an ACF. Described in detail in U.S. Pat. No. 6,083,172 |
| Kalman Saturation with Kalman Cardiac Gated Averaging | Saturation value obtained by ensemble averaging of the pulse oximetry signal synchronous with the pulse rate tracked by the ACF (or by ECG if available), where both the ensemble averaging and saturation calculations are performed in accordance with Kalman filter theory. Described in detail in U.S. Pat. No. 6,411,833. |
| Pattern Match Rate | Pulse rate determined by identification and qualification of individual pulses. Described in U.S. Pat. No. 6,836,679. |
| Long-Term Pulse Period Variability | A metric of the beat-to-beat variability of qualified pulses periods, suitable for detecting and quantifying arrhythmia. Preferably calculated with a response time of at least 50 pulses due to the episodic nature of arrhythmias. Preferably corrected for variations in the mean pulse period, for example by calculating variability from the logarithms of the pulse periods. |
| ACF Confidence Metric | A metric quantifying the likelihood that the ACF rate is within a predetermined accuracy. Examples described in detail in U.S. Pat. No. 7,302,284 |
| Pattern Match Rate Confidence Metric | A metric quantifying the likelihood that the Pattern Match Rate is within a predetermined accuracy, such as the percentage of recently detected pulses that were qualified or disqualified. |
| Kalman Saturation Variability (noise) Metric, without Kalman Cardiac Gated Averaging | An indication of the degree of correlation of the filtered IR and Red waveforms input to the Kalman filter for saturation calculationm where filtering of said waveforms does NOT include Cariac Gated Averaging.. |
| Kalman Saturation Variability (noise) Metric, with Kalman Cardiac Gated Averaging | An indication of the degree of correlation of the filtered IR and Red waveforms input to the Kalman filter for saturation calculation, where filtering of said waveforms includes Cardiac Gated Averaging. |
| ACF Signal-to-Noise Metric | Ratio of in-band (signal) to out-of-band (noise) energy from the ACF. A high value indicates that the pulse is regular and being correctly tracked by the ACF. |
| ACF Skewness (pulse shape) Metric | The skewness of the derivative of the plethysmographic waveform after filtering by the ACF. Due to the sawtooth shape of an arterial photoplethysmograph, this derivative should have a negative value if the ACF is tracking the pulse rate and the pulse rate is regular. |
| Age Metric, Kalman Saturation, without Kalman Cardiac Gated Averaing | A metric indicative of the cumulative response time of all filtering preceding and including saturation calculation that is performed without Cardiac Gated Averaging. |
| Age (noise) Metric, Kalman Saturation, with Kalman Cardiac Gated Averaging | A metric indicative of the cumulative response time of all filtering preceding and including saturation calculation that is performed with the aid of Cardiac Gated Averaging. |

TABLE 1-continued

| Signal Quality Metric | Description |
|---|---|
| Mean AC Amplitude | Indication of pulse and/or artifact amplitude. Extremely small or large values may be indicative of artifact. Described in detail in U.S. Pat. No. 6,035,223. |
| AC Amplitude Variability | Indication of variability in pulse and/or artifact amplitude. Higher values may be indicative or artifact or arrhythmia. Described in detail in U.S. Pat. No. 6,035,223. |
| IR/Red Correlation | Indication of how well correlated the AC portions of the IR and Red photoplethysmographs are. Poorer correlation may be indicative of artifact. Described in detail in U.S. Pat. No. 6,035,223. |
| DC Variability | Indication of how variable the IR photocurrent is. Higher values may be indicative of artifact. Described in detail in U.S. Pat. No. 6,035,223. |
| DC Slope | Indication of how rapidly the IR photocurrent is growing or shrinking over several seconds. Higher values may be indicative of artifact. Described in detail in U.S. Pat. No. 6,035,223. |
| Skewness (pulse shape) of IR Derivative Waveform | Indication of the shape of the pulsatile waveform. A negative skewness is typical of an arterial photoplethysmograph. Described in detail in U.S. Pat. No. 6,035,223. |
| Maximum Autocorrelation of IR Waveform | Indication of the regularity of the pulsatile waveform. Described in detail in U.S. Pat. No. 6,035,223. |
| Persistent IR-Red Phase Difference | Described in detail in U.S. Pat. App. Pub. No. 2005/0197579 |
| Frequency Ratio | Ratio of a characteristic frequency of the current signal to the frequency corresponding to the pulse-rate estimate.. |
| Amplitude Ratio | Ratio of amplitude of current pulse to long-term average of pulse amplitude. The long-term average is preferably calculated from the amplitudes of qualified pulses and averaged with a response time of at least fifty pulses. |
| Low DC Signal | Intensity of light detected by photodetector, adjusted for intensity of LED. Used to indicate whether the sensor is applied to an excessively opaque tissue site. |

TABLE 2 shows the accuracy of various neural networks trained with combinations of the above signal quality metrics, and contrasts the accuracy of an algorithm similar to that of the Nellcor N-595. Neural networks having different outputs were tested, including outputs of SpO$_2$, pulse rate (in beats per minute or BPM) and accuracy. Some entries break the data into "clean" and "noisy" subsets. The "clean" subset comprised data where the Pattern Match Rate Confidence metrics exceeded 95% (very few pulses disqualified) AND the Kalman Saturation Variability metric with Kalman Cardiac Gated Averaging was under 3 percent saturation (little or no noise). The "noisy" subset comprised data that did not meet the criteria for the "clean" subsystem. The clean and noisy subsets each represented about 50 percent of the data, and are typical of the non-motion and motion data respectively.

TABLE 2

| Algorithm | Outputs | Inputs | Accuracy (RMSD) |
|---|---|---|---|
| An algorithm similar to that of the Nellcor N-595 | SpO$_2$ | Both Kalman Saturation estimates | 7.1% for all data<br>2.1% for clean data<br>9.1% for noisy data |
| Neural net (4 hidden nodes) | SpO$_2$ | Both saturations plus all metrics | 3.6% for all data<br>2.1% for clean data<br>4.7% for noisy data<br>3.7%-4.0% when trained on half of subjects and used to predict the other half |
| Neural net (3 hidden nodes) | SpO$_2$ | Kalman Saturation w/ Kalman Cardiac Gated Averaging plus one metric from:<br>Pattern Match Rate Confidence<br>ACF Signal-to-noise<br>ACF Skewness<br>Sat Age w/ Cardiac Gated Averaging<br>Maximum Autocorrelation | 3.9%-4.0% for all data |

TABLE 2-continued

| Algorithm | Outputs | Inputs | Accuracy (RMSD) |
|---|---|---|---|
| Neural net (4 hidden nodes) | $SpO_2$ | Kalman Saturation w/ Kalman Cardiac Gated Averaging plus 3 metrics: Pattern Match Rate Confidence Pulse Period Variability Sat Variability w/ Cardiac Gated Averaging | 3.7% for all data |
| Neural net (3 hidden nodes | $SpO_2$ Accuracy | Both saturation plus all metrics | 3.1% for all data |
| Neural net (3 hidden nodes) | $SpO_2$ Accuracy | Kalman Saturation w/ Kalman Cardiac Gated Averaging plus 2 metrics: ACF Skewness Saturation Age w/ Cardiac Gated Averaging | 3.4% for all data |
| An algorithm similar to that of the Nellcor N-595 | Pulse Rate | Pattern Match Rate and Adaptive Comb Filter Rate | 9.3 BPM for all data 6.2 BPM for clean data 12.0 BPM for noisy data |
| Neural net (4 hidden nodes) | Pulse Rate | Both rates plus all metrics | 3.2 BPM for all data 0.7 BPM for clean data 4.4 BPM for noisy data |
| Neural net (3 hidden nodes) | Pulse Rate | Both rates plus 2 metrics: Pulse Period Variability ACF Confidence | 3.4 PM for all data |
| Neural net (4 hidden nodes) | Pulse Rate Accuracy | Both rates plus all metrics | 2.7 BPM for all data |
| Neural net (3 hidden nodes) | Pulse Rate Accuracy | Pattern Match Rate plus ACF Skewness Metric | 3.5 BPM for all data |
| Neural net (3 hidden nodes) | Pulse Rate Accuracy | Pattern Match Rate plus 3 metrics selected from: Pulse Period Variability ACF Confidence Pattern Match Rate Confidence ACF Signal-to-Noise ACF Skewness | 3.2 BPM for all data |

Figure 7A:
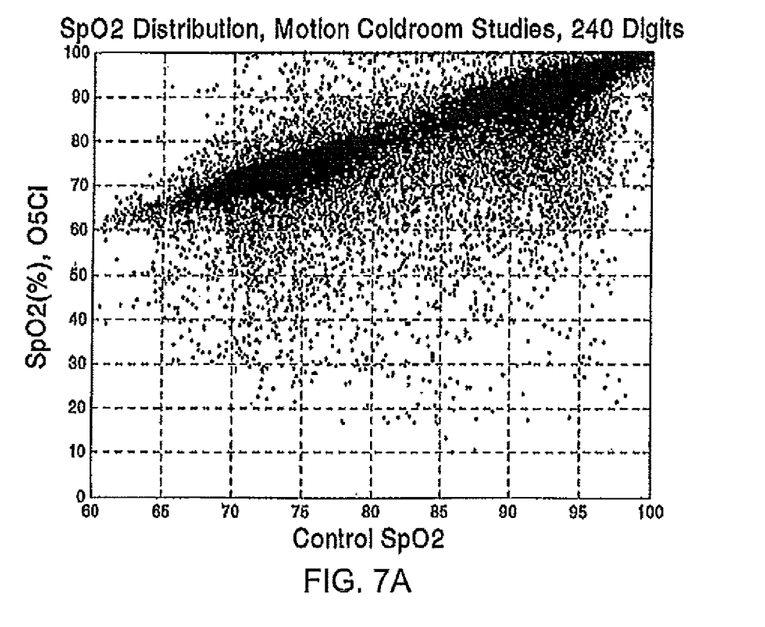
FIGS. 7A and 7B present selected results of the experiments performed.
Figure 7B:
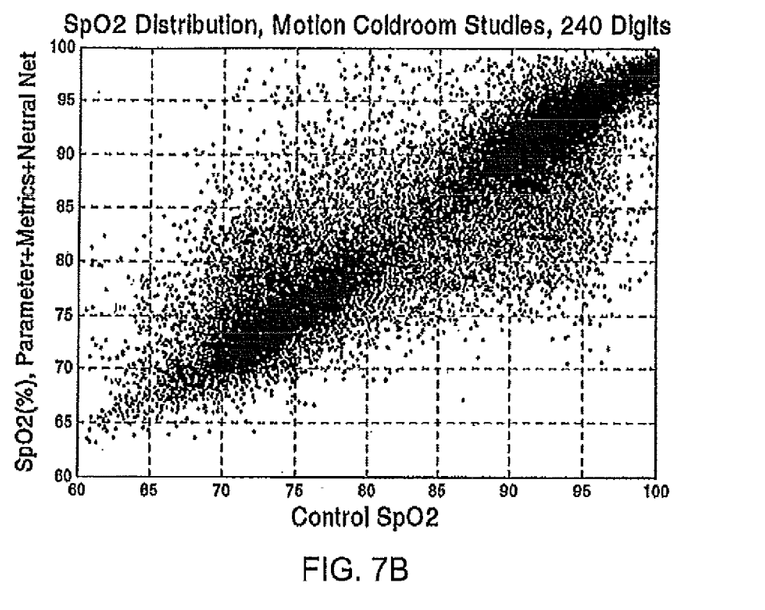

FIGS. 7A and 7B illustrate a graphical representation of selected results of the experiments performed. FIG. 7A shows the $SpO_2$ distribution, for the "noisy" half of the data, of the N-595 Saturation (line 1 of Table 2) versus the control data obtained from the non-motion hand. Note the large number of outlier points where N-595 $SpO_2$ estimates were as low as 10%. FIG. 7B shows the $SpO_2$ estimated by the neural network using both input saturation plus all metrics (line 2 of Table 2), with the Y-scale increased relative to FIG. 7A due to the substantial reduction in outliers and overall improvement in estimate quality. Each figure contains about 25,000 data points.

It will be clear that the described systems and methods are well adapted to attain the ends and advantages mentioned as well as those inherent therein. Those skilled in the art will recognize that the methods and systems described within this specification may be implemented in many different manners and as such are not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. For example, the reader will understand that alternative signal quality metrics or combining means may be used in the refinement of an estimated value of a physiological parameter and/or the accuracy of the estimated value of the parameter without departing form the spirit of the disclosure. In addition, a radial basis neural network, fuzzy logic or an ad hoc rule set could be used. Numerous other changes may be made which will readily suggest themselves to those skilled in the art and which are encompassed in the spirit of the disclosure and as defined in the appended claims.

What is claimed is:

1. A method for determining the oxygen saturation of blood of a patient comprising:
   estimating a physiologic parameter from an electronic signal;
   calculating one or more signal quality metrics of the electronic signal;
   inputting information into a neural network, wherein said input information includes one or more estimates of the physiologic parameter and at least one signal quality metric; and
   calculating with the neural network at least one output datum, wherein the output datum is representative of the oxygen saturation of the blood of the patient.

2. The method of claim 1 wherein the physiological parameter is pulsatile oxygen saturation of the blood of the patient.

3. The method of claim 1 wherein the input information comprises:
   i) the estimated physiologic parameter;
   ii) at least one signal quality metric;
   iii) data processed from the estimated physiologic parameter; and/or
   iv) data processed from the one or more signal quality metrics.

4. The method of claim 1 further comprising:
   displaying the output datum from the neural network on a display device.

5. The method of claim 1 further comprising:
   generating an alarm if the output datum from the neural network is not within an acceptable range of oxygen saturation.

6. The method of claim 1 further comprising:
   selecting the information to be input into the neural network; and
   training the neural network using the selected information.

7. The method of claim 1 wherein the signal quality metrics comprise a Kalman saturation, an adaptive comb filter (ACF) rate, a Kalman saturation calculated using Kalman Cardiac Gated Averaging, a pattern match rate, a long-term pulse period variability metric, an ACF confidence metric, a pattern match rate confidence metric, a Kalman saturation variability metric calculated without Kalman Cardiac Gated Averaging, a Kalman saturation variability metric calculated using Kalman Cardiac Gated Averaging, an ACF signal-to-noise metric, an ACF skewness (pulse shape) metric, an age metric based on the Kalman saturation calculated without Kalman Cardiac Gated Averaging, an age metric based on the Kalman Saturation calculated using Kalman Cardiac Gated Averaging, a mean AC amplitude, an AC amplitude variability metric, a IR/Red light correlation metric, a DC variability metric, a DC slope, a skewness (pulse shape) metric of IR derivative waveform, a maximum autocorrelation metric based on an IR waveform, a persistent IR-Red phase difference metric, a frequency ratio, an amplitude ratio, and/or a low DC signal metric.

8. The method of claim 1 further comprising:
   selecting the neural network from a set of neural networks based on current conditions.

9. The method of claim 8 wherein selecting further comprises:
   selecting the neural network from the set of neural networks based on a current value of one or more of the calculated signal quality metrics.

10. The method of claim 8 wherein selecting further comprises:
    selecting the neural network from the set of neural networks based on a characteristic of the patient.

11. A pulse oximeter comprising:
    a microprocessor configured for calculating an estimated value of oxygen saturation of a patient's blood based at least in part upon an electronic signal received from a sensor;
    a neural network module configured for receiving the estimated value as an input and calculating a revised value of oxygen saturation of a patient's blood using a neural network; and
    a display configured for displaying the revised value of the oxygen saturation of the patient's blood.

12. The pulse oximeter of claim 11 further comprising:
    non-transitory memory configured for storing at least one neural network including the neural network used by the neural network module to calculate the revised value.

13. The pulse oximeter of claim 12, wherein the neural network module is further configured for receiving the estimated value and at least one signal quality metric describing the electronic signal.

14. The pulse oximeter of claim 12 further comprising:
    an accuracy module configured for calculating an accuracy of the estimated value.

15. The pulse oximeter of claim 14, wherein the neural network module is further configured for receiving the estimated value and the accuracy.

16. The pulse oximeter of claim 14, wherein the neural network module is further configured for calculating a revised accuracy associated with the revised value of the oxygen saturation of the patient's blood.

17. The pulse oximeter of claim 11, wherein the neural network is a backpropagation neural network.

* * * * *